(12) United States Patent
Kettel et al.

(10) Patent No.: US 12,053,552 B2
(45) Date of Patent: Aug. 6, 2024

(54) FUNCTIONAL WOUND DRESSING

(71) Applicants: PAUL HARTMANN AG, Heidenheim (DE); UNIVERSITY OF BATH, Bath (GB)

(72) Inventors: Markus Kettel, Heidenheim (DE); Andrew Tobias Jenkins, Bath (GB); Naing Tun Thet, Bath (GB)

(73) Assignee: PAUL HARTMANN AG, Heidenheim (DE)

( * ) Notice: Subject to any disclaimer, the term of this patent is extended or adjusted under 35 U.S.C. 154(b) by 773 days.

(21) Appl. No.: 17/055,341

(22) PCT Filed: May 13, 2019

(86) PCT No.: PCT/EP2019/062216
§ 371 (c)(1),
(2) Date: Nov. 13, 2020

(87) PCT Pub. No.: WO2019/219613
PCT Pub. Date: Nov. 21, 2019

(65) Prior Publication Data
US 2021/0361822 A1    Nov. 25, 2021

(30) Foreign Application Priority Data
May 14, 2018   (EP) .................................... 18172095

(51) Int. Cl.
*A61L 15/56*   (2006.01)
*A61L 15/20*   (2006.01)
*A61L 15/60*   (2006.01)

(52) U.S. Cl.
CPC .............. *A61L 15/56* (2013.01); *A61L 15/20* (2013.01); *A61L 15/60* (2013.01);
(Continued)

(58) Field of Classification Search
CPC .......... A61L 15/56; A61L 15/20; A61L 15/60; A61L 2300/214; A61L 2300/442; A61L 2300/626; A61L 2300/802
See application file for complete search history.

(56) References Cited

U.S. PATENT DOCUMENTS

| 5,160,328 A | 11/1992 | Cartmell et al. |
| 6,238,691 B1 | 5/2001 | Huang |

(Continued)

FOREIGN PATENT DOCUMENTS

| RU | 2270646 C2 | 2/2006 |
| RU | 2276998 C2 | 5/2006 |
| WO | WO 2013/104876 A1 | 7/2013 |

OTHER PUBLICATIONS

Zhou et al., ("Development of a prototype wound dressing technology which can detect and report colonization by pathogenic bacteria" in Biosensors and Bioelectronic, 30 (2011) 67-72, provided by applicant on form 1449). (Year: 2011).*

(Continued)

*Primary Examiner* — Blessing M Fubara
(74) *Attorney, Agent, or Firm* — Leydig, Voit & Mayer, Ltd.

(57) ABSTRACT

The invention relates to a functional wound dressing being able to detect and indicate the state of the wound, in particular with regard to infections for example caused by toxins produced by bacteria such *Staphylococcus aureus* and *Pseudomonas aeruginosa*. The present wound dressing can be used in moist wound healing and contains a substance being able to absorb wound exudate from the wound and to provide moisture to the wound.

10 Claims, 4 Drawing Sheets

(52) U.S. Cl.
CPC ... *A61L 2300/214* (2013.01); *A61L 2300/442* (2013.01); *A61L 2300/626* (2013.01); *A61L 2300/802* (2013.01)

(56) References Cited

U.S. PATENT DOCUMENTS

2001/0026810 A1* 10/2001 McGhee ............... A61L 15/60
424/769
2011/0280926 A1 11/2011 Junginger

OTHER PUBLICATIONS

Stout et al., ("Glycerin-Based Hydrogel for Infection Control," in Advances in Wound Care, vol. 1, No. 1, 2011). (Year: 2011).*
Park et al., (WO 2017074093 A1, using the Eng. Trans PE2E). (Year: 2017).*
International Search Report and Written Opinion mailed Jun. 3, 2019 in PCT/EP2019/062216—13 pages.
Thet et al. (2016) "Prototype Development of the Intelligent Hydrogel Wound Dressing and its Efficacy in the Detection of Model Pathogenetic Wound Biofilms", ACS Appl. Materials Interface, vol. 8, No. 24, pp. 14909-14919 (DOI: 10.1021/acsami.5b07372).
Zhou et al., (May 12, 2010) "A Thin Film Detection/Response System for Pathogenic Bacteria" Journal of the American Chemical Society, vol. 132, No. 18, pp. 667-6570 (Abstract only).
Zhou et al. (Aug. 22, 2011), "Development of a prototype would dressing technology which can detect and report colonization by pathogenic bacteria", Biosensors and Bioelectronics, vol. 30, No. 1, pp. 67-72.
Office Action mailed Jan. 12, 2023 in corresponding Russian Patent Application RU 2020140923.

* cited by examiner

FUNCTIONAL WOUND DRESSING

CROSS-REFERENCE TO RELATED APPLICATIONS

This application is a U.S. National Stage Application filed under 35 U.S.C. § 371 of International Application No. PCT/EP2019/062216, filed May 13, 2019, which claims the benefit of and priority to. European Patent Application Serial No. 18172095.4, filed May 14, 2018, each of which is hereby incorporated by reference in its entirety.

The invention relates to a functional wound dressing being able to detect and indicate the state of the wound, in particular with regard to infections for example caused by toxins produced by bacteria such *Staphylococcus aureus* and *Pseudomonas aeruginosa*. The present wound dressing can be used in moist wound healing and contains a substance being able to absorb wound exudate from the wound and to provide moisture to the wound.

A wound can be regarded as separation of the contiguity of tissues of the skin, wherein this can be combined with a loss of substance.

The healing of wounds is based on the ability of the skin to regenerate tissue such as epithelial tissue, connective and supporting tissue. The regeneration of tissue is a complex occurrence of cell activities overlapping each other, wherein said cell activities promote the healing process step by step. An accumulation of wound exudate, which might contain inter alia blood, proteins, residues of cells, microorganisms and leucocytes, can promote the growth of bacteria. Such bacteria can be for example *Staphylococcus aureus* and *Pseudomonas aeruginosa* being present on the skin or widespread in moist milieu. This bacteria cause infection and thus delay the healing of the wound. Keeping this in mind and in order to improve the wound healing by appropriate handling or treatment, the state of the wound with regard to the grade of infections should be detected, the earlier the better.

WO 2013/104876 as well as Thet N. T. et al: "Prototype Development of the Intelligent Hydrogel Wound Dressing and Its Efficacy in the Detection of Model Pathogenetic Wound Biofilms", ACS Appl. Mater Interfaces, 2016, 8 (24) pages 14909-14919 describe the use of lipid vesicles. Said lipid vesicles contain a fluorescent dye, which is released from the vesicle at contact with toxins produced for example by bacteria such as *S. aureus* and/or *P. aeruginosa*, wherein the released dye can be detected by its fluorescence. Further, said documents describe a wound dressing using the lipid vesicles in a matrix of agarose gel. Agarose is a polysaccharide made up of the repeating unit of agarobiose, which is a disaccharide of D-galactose and 3,6-anhydro-L-galactopyranose. Agarose gel is reported to be present in an almost completely hydrated form (99%), which allows to provide water to the wound and, thus, to keep the wound humid. In turn, agarose gel seems to be improvable as far as the uptake of fluids from the wound such as exudate is concerned. Further, the wound dressing described in the above-mentioned documents has a milky-cloudy appearance and, thus, seems to be improvable with regard to the transparency. Transparency would allow an easy visual inspection of the fluorescence and, thus, an indication of the presence of bacteria and/or the state of the wound healing. Further, agarose is reported not to be stable in view of radiation usually used to sterilize a wound dressing. Thus, radiation sterilization might damage or even disintegrate such a wound dressing.

Thus, there is still a need for wound dressings capable of keeping the wound humid but simultaneously adsorbing liquid such as exudate from the wound, wherein the wound dressing further allows an easy visual inspection of the state of the wound as well as a common sterilisation via radiation.

Hence, it was an object of the present invention to overcome the above drawbacks. In particular it was an object of the present invention to provide a wound dressing with humidity-modulating properties. Especially, the wound dressing should not only provide humidity to the wound to keep it moist, but also adsorb (remove) exudate produced in the wound inhibiting the healing process. Further, the wound dressing should allow an easy visual detection of infections caused by toxins produced by bacteria such as *S. aureus, P. aeruginosa* etc. With regard thereto it should be assured that the release of the fluorescent dye is just caused by the toxins caused by bacteria and not by compounds of the wound dressing itself. Moreover, the wound dressing should maintain its integrity under common sterilization conditions such as conditions under which sterilization via radiation is carried out.

SUMMARY

The present invention has unexpectedly solved the above objectives by a new wound dressing comprising a selected hydrogel and a carrier containing fluorescent dye, wherein the hydrogel comprises a buffer, wherein the buffer substances after being dissolved in demineralized water at 37° C. form a buffer solution having a pH value of 6.0 to 9.0.

Thus, the subject of the present invention is a wound dressing comprising
  a) a hydrogel selected from starch-based hydrogel, dextran-based hydrogel, alkyleneoxid-based hydrogel, cellulose-based hydrogel, pectin-based hydrogel, alginate-based hydrogel, chitosan-based hydrogel, hyaluronic acid-based hydrogel, gellan-based, polypeptide-based hydrogel, polyakyleneoixd-based hydrogel, poly(methacrylate)-based hydrogel, poly (alkyl(methacrylate)-based hydrogel, poly(ethacrylate)-based hydrogel, vinyl polymer based hydrogel, polycaprolactam- and polycaprolactone-based hydrogel, polyurethane-based hydrogel, polyurea-based hydrogel, polyurethane-polyurea-copolymer-based hydrogel and mixtures thereof; and
  b) a carrier containing fluorescent dye,
  wherein the hydrogel comprises a buffer, wherein the buffer substances after being dissolved in demineralized water at 37° C. form a buffer solution having a pH value of 6.0 to 9.0.

BREIF DESCRIPTION OF THE DRAWINGS

Figure 7:
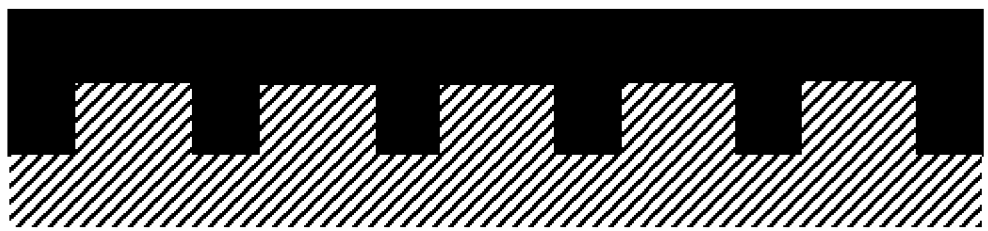
Figure 7:
Figure 7:
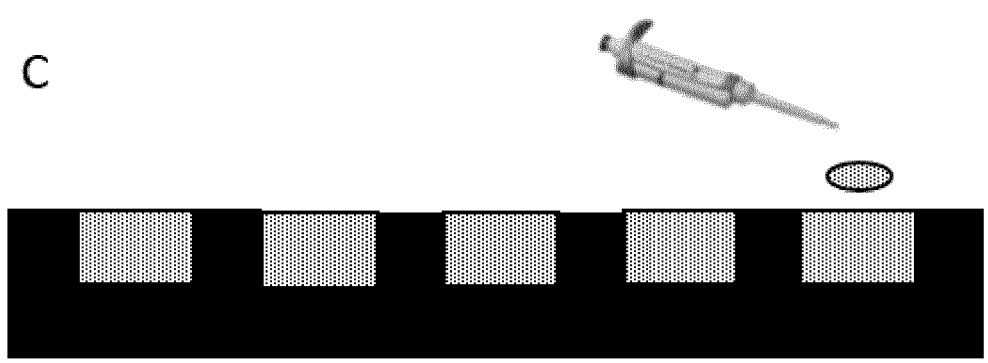

FIG. 7 illustrates the production of a wound dressing in an embodiment of the invention. Fluid hydrogel mixture is poured into a metal mould having recesses (panel A). After polymerization, the hydrogel is separated from the mould, wherein the hydrogel contains recesses (panel B). A hydrogel solution is mixed with liposomes containing carboxyfluorescein, and is used to fill the recesses in the hydrogel (panel C).

DETAILED DESCRIPTION OF THE INVENTION

The present wound dressing comprises a selected hydrogel. In line with the present application a hydrogel is referred to as a synthetic or natural polymeric material, preferably a hydrophilic synthetic or natural polymeric material, which is capable of gel formation within a liquid, preferably water. The synthetic or natural polymeric material can be regarded as a matrix or hydrogel matrix.

The selected hydrogel comprised by the present composition can be preferably based on natural polymeric material selected from starch, dextran, pectin, alginate, chitosan, hyaluronic acid, gellan, polypeptide and cellulose. Optionally, the natural polymeric material can be further processed, for example by chemical derivation such as the formation of esters and ethers or pharmaceutically acceptable salts.

Starch is a polysaccharide containing a large number of α-D-glucose units which are joined by glycosidic bonds. Starch can be produced by mot plants and used as energy storage. Starch is regarded as insoluble in cold water (23° C.) but is able to exothermically swell up by physically binding a morefold of water compared to its own weight.

Dextran is a complex branched polysaccharide containing glucose units only, wherein the chains have different number average molecular weights from 10.000 to 50.000.000 Daltons determined by gel permeation chromatography. The straight chain consists of glucose molecules being bonded by α-1,6 glycosidic linkages, while branches begin from α-1,3 linkages. Brought into contact with water, dextran forms highly viscous liquids (gels).

Pectin is a vegetable structural polysaccharide obtainable from plants such as citrus fruits. Pectin is a polysaccharide (more exactly a polyuronide) which mainly contains D-galacturonic acid units being α-1,6 glycosidicly joined. All, just a part or none of the carboxy residues of the galacturonic acid in pectin can be present in an esterified form, for example as methyl or ethyl ester.

Alginate is a polysaccharide containing homopolymeric blocks of (1-4)-linked β-D-mannuronate and α-L-guluronate (G) residues, respectively, covalently linked together in different sequences or blocks. Alginate can be present in form of its salts such as alkaline metal or earth alkaline metal salts or in esterified form such as in form of an alkyl ester, preferably methyl ester. Alginate is able to quickly absorb water to form a hydrogel. Thus, alginate can be used as gelling agent.

Chitosan is a linear biopolymer (polysaccharide) containing randomly distributed β-(1,4)-linked D-glucosamine units (deacetylated unit) and N-acetyl-D-glucosamine units, wherein the polymeric chain preferably contains more D-glucosamine units than N-acetyl-D-glucosamine units. Chitosan can be obtained from chitin by deacetylation either enzymatically or via an alkaline compound such as sodium hydroxide.

Hyaluronic acid is an important component of the connective tissue. Hyaluronic acid is a polymer which contains a disaccharide as repeating unit, wherein the chain comprises 250 to 50.000 of the disaccharide units. Said disaccharide comprises D-glucuronic acid and N-acetyl-D glucosamine being bound via a glycosidic β-(1,3) linkage. Hyaluronic acid can be present in form of its salts such as alkaline metal or earth alkaline metal salts, in particular in form of the sodium or potassium salt.

Gellan (also referred to as gellan gum) is anionic polysaccharide obtained via fermentation of carbon hydrates by a bacterium called *Pseudomonas elodea*. Gellan is a polymer containing a tetrasaccharide as repeating unit, wherein the chain comprises 250 to 50.000 of the tetrasaccharide units. Said tetrasaccharide units comprise two residues of D-glucose, one residue of L-rhamnose and a residue of D-glucuronic acid in the following order: D-glucose-D-glucuronic acid-D-glucose-L-rhamnose. A part of the D-glucose residues can be esterified with acetic acid and/or glycerol acid. Further, the D-glucoronic acid residues can be present in form of a salt, preferably in form of the potassium, sodium, magnesium and calcium salt.

A polypeptide is a chain of amino acids linked together, wherein a single polypeptide chain might make up the entire primary structure of a simple protein. More complex proteins are formed when two or more polypeptides are linked together. Polypeptides can be naturally occurring or obtained via peptide synthesis for example via the Merrifield Synthesis.

A cellulose based hydrogel is a hydrogel based on cellulose and/or its derivatives. Cellulose is a polysaccharide containing a linear chain of several hundred to many thousands of β(1→4)-linked D-glucose units. Within the present application cellulose derivatives are for example cellulose ether and cellulose ester as well as their salts. Examples of cellulose ethers are hydroxyalkyl cellulose, in particular hydroxy $C_{1-6}$-alkyl cellulose such as hydroxymethyl cellulose, hydroxyethyl cellulose, hydroxypropyl cellulose, hydroxyisopropyl cellulose and hydroxybutyl cellulose, preferably hydroxymethyl cellulose and/or hydroxyethyl cellulose. Examples of cellulose esters are carboxyalkyl cellulose, in particular carboxy $C_{1-6}$-alkyl cellulose such as carboxymethyl cellulose, carboxy ethyl cellulose, carboxypropyl cellulose, carboxybutyl cellulose and/or their salts. Preferred are carboxymethyl cellulose and carboxy ethyl cellulose and their salts, in particular the sodium salt. Further, a mixture of the mentioned compounds can be used. The number average molecular weight of cellulose and/or its derivates is 1.000 g/mol to 250.000 g/mol, preferably 5.000 g/mol to 175.000 g/mol, in particular 10.000 g/mol to 100.000 g/mol, determined with gel permeations chromatography.

The selected hydrogel comprised by the present composition can be preferably based on synthetic polymeric material selected from polyalkylene oxide-based hydrogel, poly (meth)acrylate-based hydrogel, poly(eth)acrylate-based hydrogel, poly alkyl(meth)acrylate-based hydrogel, poly alkyl(meth)acrylate-based hydrogel, vinyl polymer based hydrogel, polycaprolactam- and polycaprolactone-based hydrogel, polyurethane-based hydrogel, polyurea-based hydrogel and polyurethane-polyurea-copolymer-based hydrogel.

In a preferred embodiment the synthetic polymeric material has a number average weight of 2.500 to 250.000.000 g/mol, preferably 5.000 to 5.000.000 g/mol, in particular 50.000 to 1.000.000 g/mol.

A polyalkylene oxide is a compound which can be represented by the formula H—$(O-A)_n$—OH, wherein A is an alkylene group, preferably a linear alkylene group comprising 2 to 6 carbon atoms, in particular 2 or 3 carbon atoms.

Preferred polyalkylene oxides are polyethylene oxide (also referred to as polyethylene glycol), polypropylene oxide (also referred to as polypropylene glycol) and a copolymer from polyethylene oxide and polypropylene oxide.

Poly(meth)acrylate and poly(eth)acrylate are polymers obtained by polymerisation of the corresponding acid, i.e. (meth)acrylic and eth(acrylic) acid, respectively. Polyalkyl (meth)acrylate and polyalkyl(eth)acrylate are alkylesters, preferably alkylesters with 1 to 6 carbon atoms, in particular methyl or ethyl ester of the before-mentioned (meth)acrylic and eth(acrylic) acids, respectively.

Vinyl polymer is a polymer derived from compounds containing a vinyl group, wherein the vinyl group can be substituted or unsubstituted, preferably substituted. Substituents can be aromatic groups such as benzene, alkyl groups, preferably $C_1$ to $C_6$ alkyl groups, or other substituents such as halogens, hydroxy and nitrile. Particularly preferred is polyvinyl alcohol.

Polycaprolactam and polycaprolactone are the polymers of the corresponding caprolactam and caprolactone. Caprolactam and caprolactone can be substituted, for example with the substituents as mentioned above, or unsubstituted, preferably unsubstituted.

Polyurea is a polymer represented by the following formula

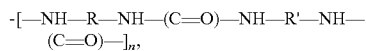

-[—NH—R—NH—(C=O)—NH—R'—NH—(C=O)—]$_n$, wherein R and R' are aliphatic or aromatic residues.

Polyurethane (PUR and PU) is a polymer composed of organic units joined by urethane (carbamate) links. Polyurethane is represented by the following formula

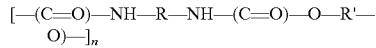

[—(C=O)—NH—R—NH—(C=O)—O—R'—O)—]$_n$ wherein R and R' are aliphatic or aromatic residues.

In a particularly preferred embodiment of the invention the selected hydrogel comprised by the present composition is a hydrogel based on a polyurethane-polyurea-copolymer. The polyurethane-polyurea-copolymer can be preferably obtained by reacting a mixture comprising a prepolymer having at least two isocyanate end groups, a diamine and a polyhydric alcohol.

It is preferred that the prepolymer having at least two isocyanate end groups has two to four isocyanate end groups, in particular two isocyanate end groups. It is further preferred that the prepolymer having at least two isocyanate end groups is an aliphatic prepolymer having at least two isocyanate end groups. In a particularly preferred embodiment the prepolymer having at least two isocyanate end groups is a prepolymer having two isophoronecyanate end groups. The prepolymer having at least two isocyanate end groups can preferably be present in the mixture in an amount of 5 to 20 wt. %, preferably 6 to 18 wt. %, in particular 8 to 16 wt. %, based on the total weight of the mixture.

The diamine comprised in the mixture can preferably be an aliphatic diamine. It is more preferred that the diamine is an alkylene oxide-based diamine. An alkyleneoxide-based diamine is a alkylene oxide whose hydroxy end groups are substituted to amine groups. An alkylene oxide-based diamine can also be referred to as polyetheramine. It is preferred that alkylene is alkylene having 1 to 6 carbon atoms, preferably 1 to 4 carbon atoms. Particularly preferred are methylene, ethylene, propylene and mixtures thereof, especially a mixture of ethylene and propylene. Diamine can preferably be present in the mixture in an amount of 5 to 70 wt. %, provided that the ratio of the isocyanote groups (of the prepolymer) to amino groups (of the diamine) is 1.15 to 1.45, preferably 1.20 to 1.40, in particular 1.25 to 1.35, based on the total weight of the mixture.

A polyhydric alcohol preferably comprises diols, triols, tetrols, pentols and hexols and mixtures thereof, more preferably diols, triol, hexols and mixtures thereof. In particular the polyhydric alcohol can be selected from glycols, especially ethylene glycol and propylene glycol, sorbitol and glycerol and mixtures thereof. The polyhydric alcohol can preferably be present in the mixture in an amount of 5 to 50 wt. %, preferably 10 to 45 wt. %, in particular 15 to 40 wt. %, based on the total weight of the mixture. Polyhydric alcohols are excellent moisturizing agents and, thus, provide a nourishing component for the skin surround the wound.

Further, the mixture can preferably comprise an inorganic salt. The inorganic salt comprises preferably an inorganic halide, in particular chloride. Further, the inorganic salt is an alkali metal or earth alkali metal salt. Examples are sodium chloride, potassium chloride, magnesium chloride and calcium chloride. In a particularly preferred embodiment the inorganic salt is sodium chloride. The inorganic salt can preferably be present in the mixture in an amount of 0 to 5 wt. %, more preferably 0.5 to 3 wt. %, in particular about 1 wt. % based on the total weight of the mixture.

As described above, the polymeric material can be regarded as a matrix or a hydrogel matrix, in particular a dry hydrogel matrix. The presently selected hydrogel matrixes can absorb water and thus, subsequently are regarded as specifically selected polymeric material-based hydrogels. The corresponding hydrogels are especially suitable to store water and then to deliver it to the wound to maintain the wound humid.

In a preferred embodiment the present hydrogel contains at least 20 wt. %, preferably at least 30 wt. %, more preferably at least 40 wt. %, in particular at least 50 wt. % of water, wherein the hydrogel preferably contains at most 90 wt. %, more preferably at most 80 wt. % of water. Thus, a wound system can be provided that on the one hand is able to provide water to maintain the wound sufficiently humid for a natural wound healing and on the other hand is able to absorb undesired fluid such as exudate from the wound.

In line with the present invention the amount of water contained in the hydrogel should be verified via DIN EN 14079, wherein the amount of water is calculated as follows:

$$W_w = \frac{W_g - W_t}{W_g} \cdot 100\% \qquad (1)$$

wherein $W_w$=weight of water in %, based on the total weight of the hydrogel, $W_g$=weight of the hydrogel $W_t$=weight of the "dry component" of the hydrogel (corresponding to the hydrogel matrix).

In the context of the invention the amount of water should be considered as water that can be theoretically released from the hydrogel. Contrary, water that is covalently bound should not be considered as belonging to the above-mentioned amount of water.

In a preferred embodiment of the invention the hydrogel is a polyurethane-based hydrogel, more preferably a polyurethane-polyurea-copolymer-based hydrogel. In a preferred embodiment the hydrogel can comprise at least 20 wt. % of water and at least 10 wt. % of polyurethane-polyureacopolymer. An alternative hydrogel comprises at least 20 wt. % of water and at least 15 wt. % of polyurethane-polyurea-copolymer.

Further, it is preferred that the polymeric syntactic material (hydrogel matrix) is formed from 6 to 60 wt. % of a prepolymer with aliphatic diisocyanate groups, 4 to 40 wt. % polyamine on a polyethylene oxide basis, at least one salt selected from sodium chloride, potassium chloride, magnesium chloride, calcium chloride or mixtures thereof and at least 20 wt. % of water.

Alternatively, it is preferred that the polymeric synthetic material (hydrogel matrix) is formed from 6 to 30 wt. % of a prepolymer with aliphatic diisocyanate end groups, 4 to 20 wt. % polyamine on a polyethylene oxide basis, at least one salt selected from sodium chloride, potassium chloride, magnesium chloride, calcium chloride or mixtures thereof and at least 30 wt. % of water.

Particularly it is preferred that the polymeric synthetic material (hydrogel matrix) is formed from 6 to 20 wt. % of a prepolymer with two isophorone cyanate end groups, 4 to 15 wt. % of diamine on a polyethylene oxide basis, 0.5 to 15 wt. % of a salt selected from sodium chloride, potassium chloride, magnesium chloride, calcium chloride or mixtures thereof and at least 40 wt. % water.

In a preferred embodiment the hydrogel has a thickness of 0.1 to 5.0 mm, more preferably 0.3 to 4.0 mm, in particular 0.5 to 3.0 mm.

The hydrogel comprised by the present wound dressing comprises a buffer, wherein the buffer substances after being dissolved in demineralized water form a buffer solution having a pH value of 6.0 to 9.0, preferably 6.2 to 8.8, more preferably 6.4 to 8.6 and in particular 6.6 to 8.4.

The term buffer substances as used in the present invention designates a mixture of chemical substances whose pH value does not change upon addition of an alkaline or acidic compound as much as in an unbuffered system. Generally, the effect of the buffered system is based on the formation of the corresponding weak bases or acid upon addition of oxonium or hydroxide ions. The obtained weak bases or acids show just a minor tendency to dissociate such that they just contribute little to the concentration of oxnonium or hydroxide ions.

The buffer substances are preferably non-toxic, skin-friendly and physiologically harmless compounds. The pH value of the compound arises upon resolving said compound in demineralized water from the balance of the protolysis of the compound. The pH value can be calculated with a good approximation by the Henderson-Hasselbalch equation. In a wound dressing according to the invention the pH value of the corresponding solution, which arises from resolving the puffer substances in demineralized water, is not calculated but measured. For such a measurement 0.1 mol of buffer substance(s) was completely dissolved at 37° C. under stirring in one liter of demineralized water. The pH value of the obtained buffer solution can be measured with a commercially available pH meter based on potentiometry such as Labor-Daten-pH-Meter CG841 (Schott Geräte GmbH) with a glass electrode "Flushtrode" (Hamilton Messtechnik GmbH), wherein the pH meter should be calibrated via commercially available calibration solutions prior to use.

Examples of buffer substances as comprised in the wound dressing according to the invention are dihydrogen phosphate/phosphate buffers, bicarbonate/carbonate buffers, hydrogensulfate/sulfate buffers, lactic acid/lactate, glyceric acid/glycerate, gluconate acid/gluconate, acetic acid/acetate, citric acid/citrate, benzoic acid/benzoate, aconitic acid/aconitate, glutaric acid/glutarate, tartaric acid/tartrate, mallow/malate, succinic acid/succinate and glutamic acid/glutamate and buffers based on alkaline organic compounds such as primary, secondary or tertiary amines or mixtures thereof.

In a preferred embodiment the buffer is based on an alkaline organic compound, more preferably the buffer comprises a 4-(2-hydroxyethyl)-1-piperazinethane sulfonic acid. 4-(2-hydroxyethyl)-1-piperazinethane sulfonic acid is represented by the following chemical formula:

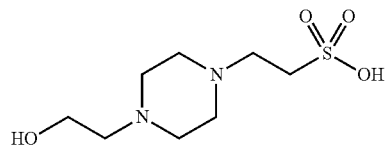 [SMILES: O=S(=O)(O)CCN1CCN(CCO)CC1]

In a further preferred embodiment the hydrogel contains substances which, when dissolved in demineralized water at 37° C., form a solution exhibiting a pH value of less than 6, amphiphilic substances and/or alcohol in an amount of 0 to 10 wt. %, preferably in an amount of 0.1 to 5 wt. %, in particular 0.2 to 2 wt. %. In a particularly preferred embodiment the amount of these substances is as small as possible, in particular 0.

Substances which when dissolved in demineralized water at 37° C. form a solution exhibiting a pH value of less than 6 can be regarded as acidic substances. The pH of the acidic substances is determined as described above. These substances are for example organic acids such as acetic acid, propionic acid, butyric acid, valeric acid, caproic acid, glycolic acid, lactic acid, pyruvic acid, alpha-ketoglutaric acid, benzoic acid, salicylic acid, acetylsalicylic acid, succinic acid, ascorbic acid, oxalic acid, citric acid, and polyacrylic acid, as well as enolic compounds such as phenol, as well as fatty acids such as caprylic acid, capric acid, lauric acid, myristic acid, palmitic acid, stearic acid, arachidic acid, behenic acid, lignoceric acid, cerotic acid, linoleic acid, myristoleic acid, palmitoleic acid, linolenic acid, arachidonic acid, erucic acid, docosahehaxanoic acid, as well as amino acids, in particular proteinogenic amino acids such as L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophane, L-tyrosine, L-valine, L-selenocysteine, L-pyrrolysine, furthermore their D-enantiomers and non-proteinogenic amino acids.

Amphiphilic compounds, often also referred to as surfactants, are composed of a non-polar and a polar part. The non-polar part can be for example an alkyl chain or an alkyl phenyl group.

The polar part of the amphiphilic compound can be composed of various functional groups being suitable to classify the surfactant into the following four categories: anionic amphiphilic compounds, cationic amphiphilic compounds zwitterionic amphiphilic compounds and non-ionic amphiphilic compounds. Particularly preferred are non-ionic amphiphilic compounds having for example one or a plurality of hydroxy or ether group(s) or combinations thereof.

Examples of non-ionic amphiphilic compounds are fatty alcohols, polyoxyethylene glycol phenyl ethers, polyoxypropylene glycol alkyl ethers, glucoside alkyl ethers, polyoxyethylene glycol sorbitan alkyl ester, sorbitan polyoxyethylene glycerol esters, polyetherramines, polyoxyethylene sorbitol esters, polyoxyethylene sorbitan esters, polyoxyethylene esters, glycerol monoesters, glycerol diesters, polyvinyl or mixtures thereof. Preferred are polyetheramine (also known as Jeffamine®) and polyethylene glycol phenyl ether such as polyethylene glycol p-(1,1,3,3-tetramethylbutyl)-phenyl ether (also known as Triton™ X-100). Alternatively preferred is free Jeffamine®. Free Jeffamine® can be referred to as Jeffamine® in its free form; i.e. not in form of an acidic or basic addition salt nor bonded to another molecule Alcohols are organic compounds in which at least one carbon atom is bound to a hydroxyl group as unique functional group. The alcohol can be a polyhydric alcohol, preferably a diol or a triol, i.e. two or three carbon atoms are bound to a hydroxy group, respectively. In a preferred embodiment the alcohol comprises 1 to 12 carbon atoms, preferably 2 to 9 carbon atoms, more preferably 3 to 6 carbon atoms.

Examples of alcohol are methanol, ethanol, propanol, isopropanol, hexanol, glycol, diethylene glycol, dipropylene glycol, hexane-1,6-diol, sorbitol and glycerol, in particular diethylene glycol, dipropylene glycol and glycerol.

The wound dressing according to the invention comprises a carrier containing fluorescent dye.

The carrier can be regarded as a medium providing a fluorescent dye to the wound dressing. The carrier is preferably in form of a capsule, wherein said capsule encapsulates a fluorescent dye and wherein said capsule ensures that said dye is not released from the capsule until in contact with substances such as toxins produced for example by bacteria such as S. aureus and/or P. aeruginosa. It is further preferred that, as long as the dye is encapsulated completely in an undamaged capsule, no coloration of the dye upon excitation with the corresponding excitation wavelength of the dye can be detected outside the capsule.

In a preferred embodiment the carrier is a liposome. A liposome can be considered as vesicle, preferably a spherical vesicle that is formed by at least one lipid bilayer.

Lipids can be used as structural components in cell membranes, as energy reservoir or signaling molecules. Lipids can be regarded as substances of substantially biological origin wherein at least a part of the lipid is non-polar and thus soluble in non-polar solvents such as pentane, hexane and benzene. Nevertheless, most of the lipids are amphiphilic, i.e. apart from the before-mentioned non-polar, hydrophobic part they comprise a polar hydrophilic part, in particular a hydrophilic end group. Generally, lipids can be categorized in the following groups: triglycerides such as fats and oils, waxes, sphingolipids, lipopolysaccharides, fatty acids, phospholipids and isoprenoids such as steroids and carotenoids.

In a preferred embodiment the lipid bilayer of the liposome contains two amphiphilic lipids such as sphingolipids, fatty acids, phospholipids and isoprenoids such as sterols. Preferred are phospholipids, sterols and 10,12-tricosadinoic acid.

Phospholipids are a group of lipids containing a phosphate group. Due to their chemical structure, phospholipids comprise two groups, namely glycerophospholipids (also referred to as a phosphoglyceride with glycerin as base structure) and sphingomyelins being a phosphor-containing sphingolipid derived from sphingosine.

Sterols (also referred to as steroid alcohols) are represented by the following base structure

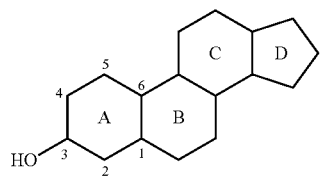

Sterols can for example be produced by some bacteria and the most familiar type is cholesterol, which is vital to cell membrane structure and functions as a precursor to fat-soluble vitamins and steroid hormones. Further examples are phytosterols such campesterol, sitosterol and stigmasterol, as well as ergosterol being present in the cell membrane of fungi.

10,12-tricosadinoic acid is a linear carboxylic acid having 23 carbon atoms and two triple bonds at positions 10 and 12.

In a preferred embodiment the liposome comprises
a) at least one of 1,2-dipalmitoyl-sn-glycero-3-phosphocholine (also referred to as DPPC), 1,2-distearyl-sn-glycero-3-phosphocholine, 1,2-dipalmitoyl-sn-glycero-3-phosphoethanolamine (also referred to as DPPE), 1,2-di stearyl-sn-glycero-3-phosphoethanolamine and 10,12-tricosadiynoic acid (also referred to as TCDA); and
b) a sterol.
More preferably the liposome comprises
a) 1,2-dipalmitoyl-sn-glycero-3-phosphocholine, 1,2-dipalmitoyl-sn-glycero-3-phosphoethanolamine and 10,12-tricosadiynoic acid; and
b) cholesterol.

Figure 1:
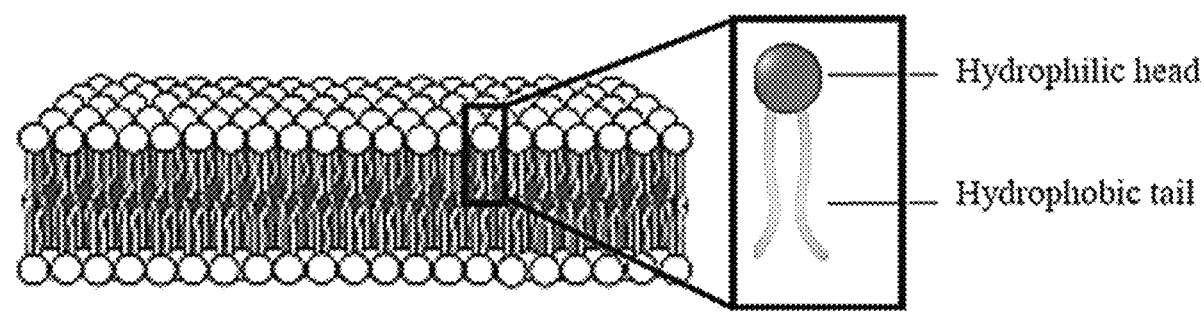
FIG. 1 shows an exemplary structure of a lipid bilayer in an embodiment of the invention.
Figure 2:
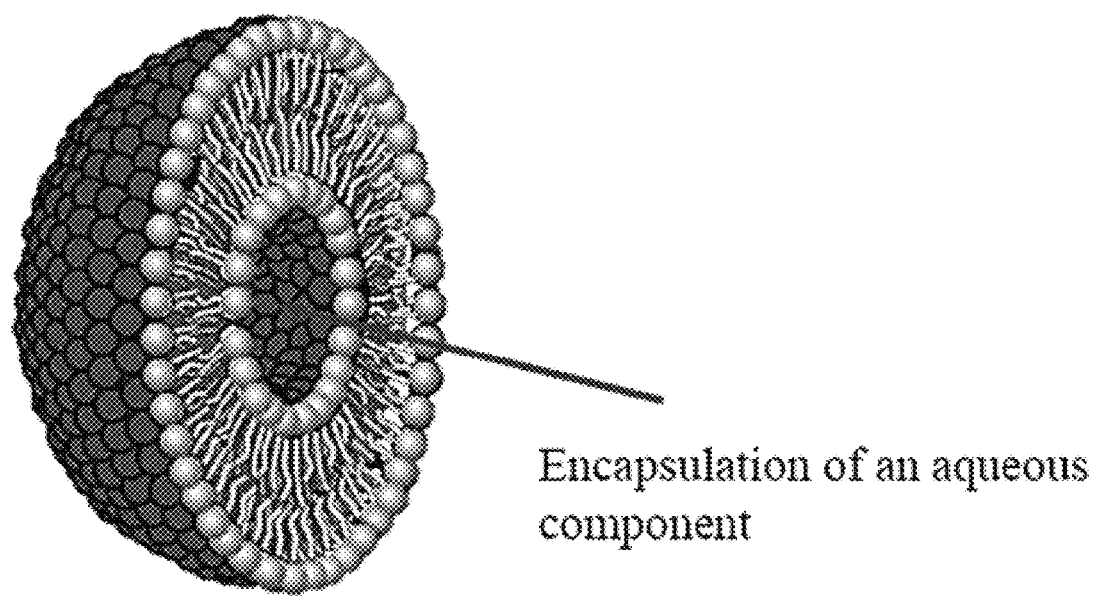
FIG. 2 shows an exemplary structure of a liposome able to encapsulate an aqueous component.

In a polar solvent a lipid bilayer is preferably formed by two lipids which are orientated such that the corresponding hydrophobic parts of the lipids are directly faced to each other and the corresponding hydrophilic parts are at the far ends of the bilayer. An exemplary structure of the lipid bilayer and the liposome are shown in FIGS. 1 and 2, respectively.

It turned out that the lipid bilayers of the liposome are formed by phospholipids such as 1,2-dipalmitoyl-sn-glycero-3-phosphocholine and 1,2-dipalmitoyl-sn-glycero-3-phosphoethanolamine and that 10,12-tricosadiynoic acid and cholesterol enhance the stability of the liposome.

As indicated above the wound dressing according to the present invention comprises a carrier containing (encapsulating) a fluorescent dye.

A fluorescent dye is a fluorescent chemical compound able to re-emit light upon excitation. It is particularly preferred that the fluorescent dye is excited with a wavelength in the UV range, preferably 100 to 380 nm, more preferably 200 to 300 nm, in particular about 250 nm, especially 254 nm. It is further preferred that the re-emitted light has a wavelength in the visible range, preferably from 400 to 750 nm, more preferably from 500 to 600 nm, in particular about 520 nm, especially 517 nm.

Fluorescent dyes are often grouped into classes such as acridine dyes, cyanine dyes, fluorone dyes, oxazine dyes, phenanthridine dyes and rhodamine dyes. Preferred are fluorone dyes.

In a preferred embodiment of the invention the fluorescent dye belongs to the group of xanthenes bearing at least one hydroxy group at the xanthene skeleton. Fluorescent dyes based on a xanthene system bearing at least one hydroxy group at the xanthene skeleton are for example eosins such as eosin B and eosin Y and fluorescein dyes such as 6-carboxyfluorescein (also referred to as carboxyfluorescein), 2,7-dichlorofluorescein and fluorescein.

In a particularly preferred embodiment the fluorescent dye is fluorescein or carboxyfluorescein, especially carboxyfluorescein.

Figure 3:
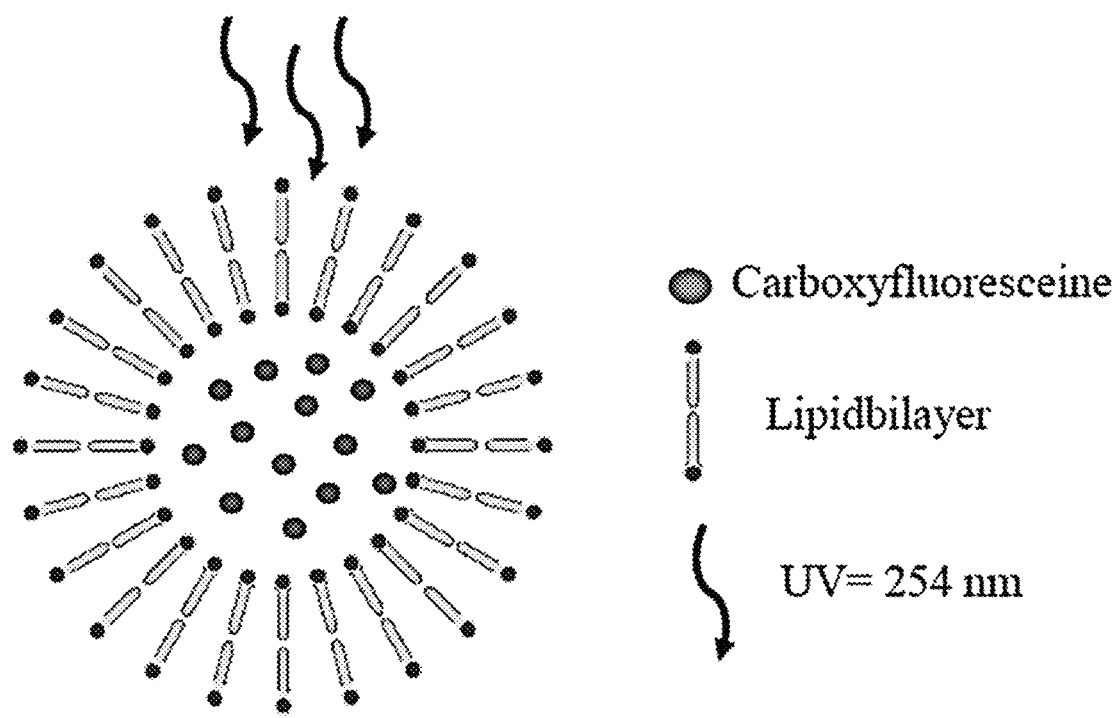
FIG. 3 shows an exemplary structure of fluorescent dye encapsulated in a lipid bilayer and excited at wavelength of 254 nm.
Figure 4:
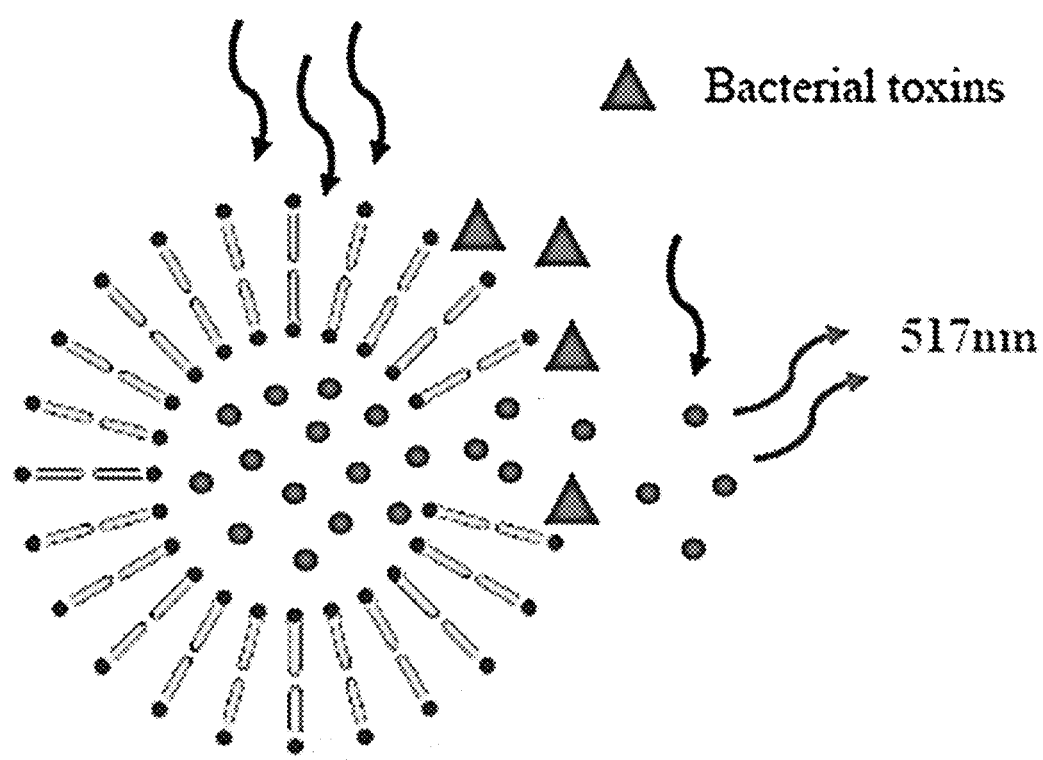
FIG. 4 shows an exemplary structure of fluorescent dye released from a lipid bilayer damaged by bacterial toxins.

An exemplary structure of fluorescent dye, encapsulated in high concentrations in the bilipid layer of the carrier, and excited at 254 nm is shown FIG. 3. As can be seen from said FIG. 3, no fluorescent dye is released from the carrier (undamaged capsules of the lipid bilayer) and, thus, no visible light can be detected. Contrary, in the presence of bacterial toxins the lipid bilayer is damaged, the fluorescent dye can be released from the capsule and thus, the dilution of the florescent dye in the hydrogel matrix takes place, which can be detected as visible light (see FIG. 4).

In a preferred embodiment of the invention the specifically selected hydrogel and the carrier containing fluorescent dye comprised by the present wound dressing are linked to each other, i.e. there are no further layers between them. In one embodiment, the carrier containing fluorescent dye is preferably applied onto the specifically selected hydrogel. In a more preferred embodiment the carrier containing fluorescent dye is embedded in the specifically selected hydrogel. Embedded can be referred to as being at least partially surrounded by the specifically selected hydrogel. For example, the hydrogel can be provided with recesses such as holes in which the carrier containing fluorescent dye can be filled or incorporated.

Experimental Part

Analytical Methods:
Determination of the pH-Value of the Hydrogel

To determine the pH value of the prepared hydrogels, a sample with a diameter of 35 mm was punched from the hydrogel and the starting weight of the sample was determined. Together with the fivefold amount of demineralized water the sample was transferred to a beaker and covered with a glass. The sample was incubated at 23° C. (room temperature) for 18 hours and after that period the hydrogel was removed from the sample and the pH value of the remaining liquid was determined in triplicate.

Determination of the Absorption Capacity of the Hydrogel

An important factor in modern wound treatment is creating and maintaining a moist wound environment while at the same time wound exudate is adsorbed and encapsulated in the wound dressing. For the characterization of the hydrogels regarding their absorption capacities, the amount of water uptake into the hydrogel is assessed at different points in time.

In this context, samples measuring 30 mm×30 mm are punched from the gels and their starting weight is determined. Then, the samples are put into beakers and covered with 120 ml demineralized water. The samples are stored at room temperature and taken out of the water at the different testing times (t=2 h, 4 h, 6 h, 8 h, 24 h, 30 h). Then, they are put on a paper towel for five seconds per side to eliminate excess water before the gels are weighed.

Since the samples have different starting weights, the increase in weights [g] is considered for a better comparability. Each sample is examined in triplicate. The absorption capacity is calculated using the following Formula:

$$W_A \; [g/g] = \frac{M_1 - M_0}{M_n}$$

$W_A$=water absorption capacity [g/g]
$M_0$=starting weight of the sample [g/g]
$M_1$=sample weight at time $t_x$ [g/g]

Determination of the Desorption Capacity of the Hydrogel

By maintaining a moist wound, the wound healing process is positively influenced. This is why one of the many requirements a wound dressing has to fulfil is the capacity to release moisture over an extended period of time.

This property is tested by measuring the desorption capacity of the hydrogels. For this test, samples measuring 30 mm×30 mm are punched from the gels and their starting weights are determined. Then, the samples are stored in a climate cabinet at a temperature of 32° C. and a relative humidity of 50% until each of the testing times. At the texting times (t=2 h, 4 h, 6 h, 8 h, 24 h, 30 h) the samples are taken from the climate cabinet and weighed again to determine weight loss or moisture loss over the time. The samples are examined in triplicate. Due to the different starting weights of the samples, the weight ratio of the samples at the different times is calculated using the following Formula for a better comparability.

$$W_D \; [g/g] = \frac{M_1}{M_n}$$

$W_D$=water desorption capacity [g/g]
$M_0$=starting weight of the sample [g/g]
$M_1$=sample weight at time $t_x$ [g/g]

Preparation of the Wound Dressing
1.1 Hydrogel

For the preparation of the hydrogel two separate aqueous liquids A and B were prepared as follows.

Aqueous Liquid A:

Sodium chloride (6.24 g; 0.107 mol) and 2-(4-(2-hydroxyethyl)-1-piperazinyl)-ethane sulfonic acid (1M HEPES in sterilized waster; 10 g) were added to sterilized and demineralized water (990 ml) and stirred for five minutes at 23° C. to form buffer solution 1. Buffer solution 1 (767.5 g) and Jeffamin-Mix (50 wt. % Jeffamin and 50 wt. % water; 132.5 g) were mixed at 23° C. under stirring for five minutes to form aqueous liquid A (900 g).

Aqueous Liquid B:

Aqueous solution B is an aliphatic isocyanate prepolymer in water (isophorone diisocyanate in water, available under the name Aquapol from Carpenter; 900 g).

The preparation of the hydrogel was conducted by the pilot casting plant B100. Aqueous liquids A and B as prepared above were filled into the casting plant's two cartridges, respectively. To ensure an exact dosage and reproducibility the launch was started not before 12 hours after the filling of the cartridges. By doing this, inaccuracies for example due to bubbles can be prevented. The content of the cartridges was transferred via a pump through different tubes in a mixing chamber, wherein a ratio of aqueous liquid 2 to aqueous liquid 1 was adjusted to 1.5:1. In the mixing chamber the two components were stirred by a mixer and the reaction took place. The not completely polymerized hydrogel was released from the mixing chamber and transferred to petri plates, where a complete curing took place.

Figure 5:
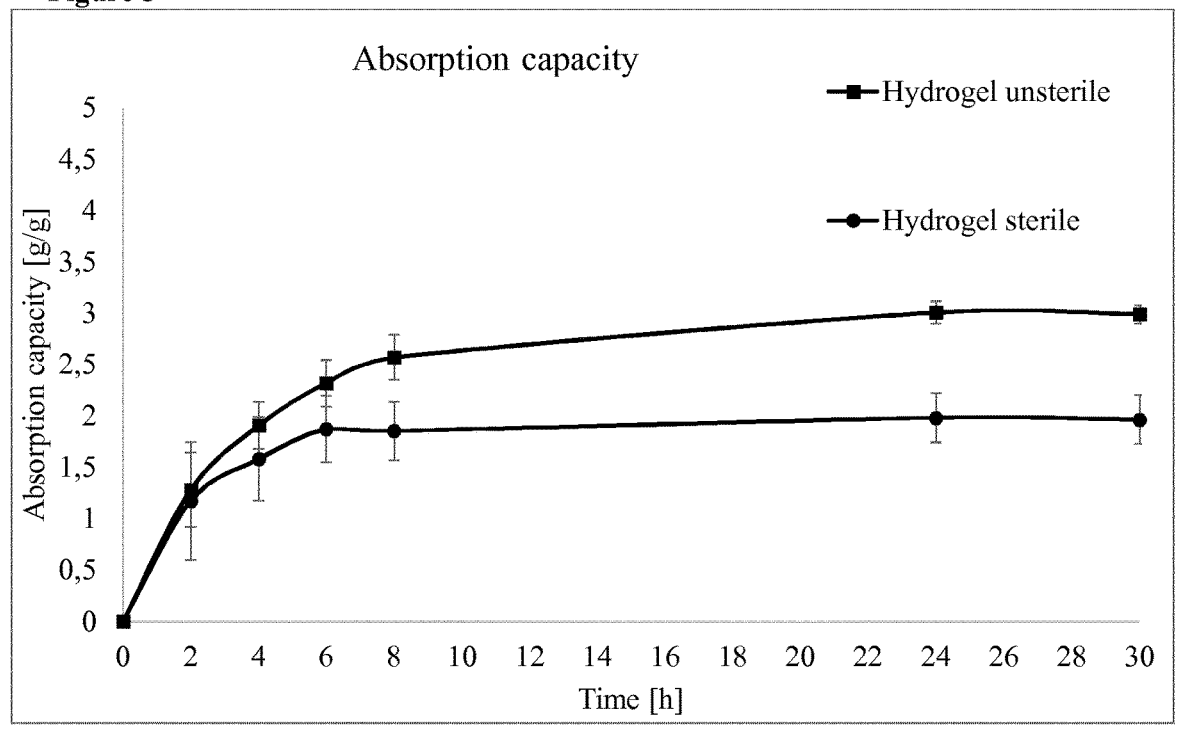
FIG. 5 is a graph showing the adsorption capacity of a hydrogel in an embodiment of the invention.
Figure 6:
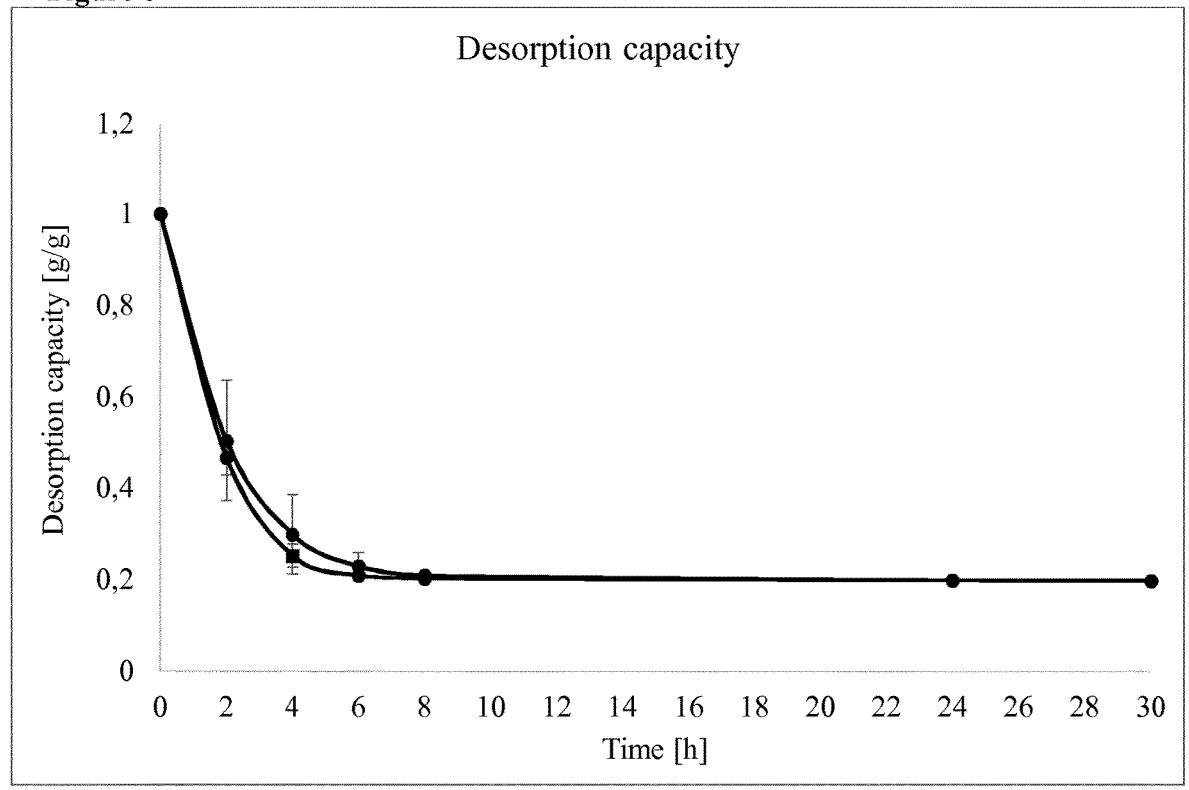
FIG. 6 is a graph showing the desorption capacity of a hydrogel in an embodiment of the invention.

Properties:
pH value of the obtained hydrogel: 8.45
Adsorption capacity of the obtained hydrogel: see FIG. 5
Desorption capacity of the obtained hydrogel: see FIG. 6

As can be seen from FIGS. 5 and 6 most water absorption as well as desorption occurs during the first eight hours; i.e. the present hydrogel is able to keep the wound moist as well as to adsorb wound exudate.

1.2 Carrier Containing Fluorescent Dye

For the carrier system the stock solutions with a concentration of 100 mM of 1,2-dipalmitoyl-sn-glycero-3-phosphocholine (DPPC), 1,2-dipalmitoyl-sn-glycero-3-phosphoethanolamine (DPPE), 10,12-tricosadiynoic acid (TCDA) and cholesterol in chloroform were prepared.

Lipid Film:

2120 µl of DPPC stock solution, 80 µl of DPPE stock solution, 1000 µl of TCDA stock solution and 800 µl of cholesterol stock solution were mixed in a vessel under stirring for five minutes. After the removal of chloroform via nitrogen gassing a lipid film was obtained. To completely remove the chloroform, the obtained product was dried for 60 minutes in a vacuum desiccator at 150 mbar.

Fluorescent Dye Solution

To carboxyfluorescein (1877 mg), sodium chloride (58 mg) and sodium hydroxide (540 mg) and a sterilely filtrated HEPES buffer solution (0.01 M) in water were added to obtain 100 ml of fluorescent dye solution.

The lipid film as obtained above was dissolved in 20 ml of the fluorescent dye solution under stirring at 70° C. for 10 minutes. The lipid mixture was freeze in liquid nitrogen and thawed at 70 C. After performing three freeze-thaw cycles, the mixture was extruded by an extruder (LiposoFast LF-50 by Avestin) at 50° C. and a pressure of 20 bar with three subsequent extrusion operations of the mixture. The carboxyfluorescein encapsulated by the carrier was purified via a Sephadex column with HEPES solution (0.01 M) as eluent, wherein particles of the encapsulated fluorescein pass the column faster than not encapsulated fluorescein, to obtain liposome containing (encapsulating) carboxyfluorescein. Liposomes were stored at 4 C for up to 120 hours before UV crosslinking. Liposomes were then transferred into quartz UV cuvettes and crosslinked under UV-C light with a total dose of 90 Wcm$^{-2}$.

1.3 Wound Dressing

To produce a wound dressing with the indicated properties the liposomes were integrated into the hydrogel as follows.

Still fluid hydrogel mixture was poured into a metal mould having recesses (Step A of FIG. 7) After the completion of the polymerization, the hydrogel was separated from the mould, wherein the hydrogel contains recesses (Step B of FIG. 7).

Further, a 0.7% solution of hydrogel in HEPES solution (0.01 M) was prepared under stirring at 43° C. for 5 minutes. Two parts per volume of this solution were mixed with one part per volume of the liposome containing carboxyfluorescein and stirred for two minutes to obtain the filling for the recesses of the hydrogel (Step C of FIG. 7). After filling the recesses of the hydrogel with the above-described filling mixture (30 µl), the filling mixture was cured at 23° C. (RT). The converted dressings were sterilized with β-Radiation using 25 kG.

The invention claimed is:

1. A wound dressing comprising:
    a) a polyurethane-polyurea-copolymer-based hydrogel; and
    b) a carrier containing fluorescent dye,
    wherein the hydrogel comprises a buffer, wherein the buffer after being dissolved in demineralized water at 37° C. forms a buffer solution having a pH value of 6.0 to 9.0.

2. The wound dressing according to claim 1, wherein the buffer comprises 4-(2-hydroxyethyl)-1-piperazineethanesulfonic acid.

3. The wound dressing according to claim 1, wherein the hydrogel contains substances which at 37° C. in demineralized water exhibit a pH value of less than 6, amphiphilic substances and/or alcohol in an amount of 0 to 10 weight percent.

4. The wound dressing according to claim 3, wherein the substances exhibiting a pH value of less than 6 in demineralized water at 37° C. comprise organic acids, enolic compounds, fatty acids or amino acids.

5. The wound dressing according to claim 3, wherein amphiphilic substances comprise polyethylene glycol p-(1,1,3,3-tetramethylbutyl)-phenyl ether and/or polyetheramine.

6. The wound dressing according to claim 3, wherein the alcohol comprises diethylene glycol, dipropylene glycol and glycerol.

7. The wound dressing according to claim 1, wherein the carrier is a liposome.

8. The wound dressing according to claim 7, wherein the liposome comprises:
    a) at least one of 1,2-dipalmitoyl-sn-glycero-3-phosphocholine, 1,2-distearyl-sn-glycero-3-phosphocholine, 1,2-dipalmitoyl-sn-glycero-3-phosphoethanolamine, 1,2-distearyl-sn-glycero-3-phosphoethanolamine and 10,12-tricosadiynoic acid; and
    b) a sterol.

9. The wound dressing according to claim 1, wherein the fluorescent dye belongs to the group of xanthenes bearing at least one hydroxy group at the xanthene skeleton.

10. The wound dressing according to claim 9, wherein the fluorescent dye is fluorescein or carboxy fluorescein.

* * * * *